United States Patent
Doiron et al.

[11] Patent Number: 5,957,917
[45] Date of Patent: Sep. 28, 1999

[54] TRANSLUMINAL HYPERTHERMIA CATHETER AND METHOD FOR USE

[75] Inventors: Daniel R. Doiron, Santa Ynez; Hugh L. Narciso, Jr., Santa Barbara, both of Calif.

[73] Assignee: Miravant Systems, Inc., Santa Barbara, Calif.

[21] Appl. No.: 08/934,537

[22] Filed: Sep. 22, 1997

Related U.S. Application Data

[63] Continuation of application No. 08/727,171, Sep. 20, 1996, abandoned, which is a continuation of application No. 08/375,468, Jan. 20, 1995, abandoned, which is a continuation of application No. 08/039,378, Mar. 30, 1993, abandoned.

[51] Int. Cl.$^6$ .................................................. A61B 17/36
[52] U.S. Cl. .................................................. 606/15; 606/17
[58] Field of Search .................................. 606/7, 13–16, 606/27–30; 607/89, 104; 604/22

[56] References Cited

U.S. PATENT DOCUMENTS

| | | | |
|---|---|---|---|
| 3,924,628 | 12/1975 | Droegemueller et al. | 606/20 |
| 4,336,809 | 6/1982 | Clark | 606/15 |
| 5,007,437 | 4/1991 | Sterzer | 607/138 |
| 5,019,075 | 5/1991 | Spears et al. | 606/7 |
| 5,190,540 | 3/1993 | Lee | 606/27 |
| 5,207,669 | 5/1993 | Baker | 606/16 |
| 5,207,672 | 5/1993 | Roth et al. | 606/7 |
| 5,269,777 | 12/1993 | Doiron | 606/16 |
| 5,281,215 | 1/1994 | Milder et al. | 606/20 |
| 5,292,320 | 3/1994 | Brown et al. | 606/17 |
| 5,415,654 | 5/1995 | Daikuzono | 606/15 |
| 5,431,648 | 7/1995 | Lev | 606/27 |

*Primary Examiner*—Michael Peffley
*Attorney, Agent, or Firm*—Bryan Cave LLP; Michael G. Petit

[57] ABSTRACT

A catheter and a method for using the catheter for the transluminal hyperthermic treatment of target tissue is presented. The catheter comprises an elongate tubular member having two coolant circulating lumens and an optical waveguide coextensive therewith, the proximal end of the optical waveguide being adapted to receive light from a light source and the distal end of the optical waveguide terminating in a diffuser tip. The diffuser tip provides a means for radially distributing treatment light from the light source to tissue adjacent to the distal tip of the catheter to heat the tissue. A transparent, inflatable balloon surrounds the diffuser tip. The inflatable balloon permits the flow of an optically transparent coolant around the diffuser tip to cool the tissue immediately adjacent to the diffuser tip to prevent overheating. A method of using the device for the transurethral treatment of benign prostate hypertrophy is presented as an example.

24 Claims, 8 Drawing Sheets

TRANSLUMINAL HYPERTHERMIA CATHETER AND METHOD FOR USE

CROSS REFERENCE TO RELATED APPLICATIONS

This is a continuation of application Ser. No. 08/727,171 filed Sep. 30, 1996 now abandoned, which is a continuation of application Ser. No. 08/375,468 filed on Jan. 20, 1995 now abandoned, which is a continuation of application Ser. No. 08/039,378 filed on Mar. 30, 1993 now abandoned.

BACKGROUND OF THE INVENTION

1. Field of the Invention

This invention relates to a catheter for diagnostic procedures such as transillumination or for therapeutic procedures such as inducing localized hyperthermia and/or photodynamic therapy in a patient and, more particularly, to a catheter for the transluminal or intersitial delivery of heat to tissue.

2. Prior Art

The use of light sources such as lasers has become common in the medical industry. As new, higher power light sources are created providing wavelengths useful for medical applications, the indications for use have increased dramatically. One such application is the delivery of diffuse light energy in energy densities sufficient to cause hyperthermia (elevated tissue temperature), photocoagulation (to weld or destroy tissue depending upon the degree of temperature increase), inducing a photodynamic/photobiological effect or performing diagnostic transillumination for imaging tissue. Current art light delivery devices are available to either diffuse or focus light in a forward direction to effect a light/tissue interaction. One limitation of these devices is that the tissue being heated develops a temperature gradient which is greatest at the interface closest to the light delivery system and decreasing with the depth of the tissue as described by thermal and light diffusion theory. Certain medical applications require a temperature field much different than this model.

Adjunctive hyperthermia, the use of deep heating modalities to treat hyperproliferating cells such as tumors, is finding increasing use for synergistically improving the effectiveness of Photodynamic Therapy (PDT), chemotherapy and radiative therapy in cancer treatment. Unfortunately, current hyperthermia devices for intraluminal delivery are not able to deliver localized heat to a target tissue located adjacent to a tubular tissue without damaging the luminal wall of the tubular tissue. In addition to the above described thermal field problem, prior art intraluminal, optically-induced hyperthermia devices cannot sufficiently couple the light energy out to the target tissue. As the light energy or power in the delivery device increases, the greater the chance that the delivery device will fail. Cooling the delivery device also permits the efficient coupling of the light energy out of the delivery device enabling the operation of the light guide at much greater power levels.

It is, therefore, desirable that a catheter is available which provides intraluminal delivery of light to a target tissue adjacent to the lumen which produces a thermal gradient which is substantially uniform in the target tissue or at least not excessive at the interface which is closest to the delivery device and which has the capacity to handle high power when required.

SUMMARY OF THE INVENTION

It is an object of this invention to provide a catheter for the transluminal delivery of optical energy to target tissue adjacent to a tubular tissue member without undue heating of the wall of the tubular tissue immediately adjacent the catheter.

It is yet another aspect of this invention to provide a catheter for delivering light to target tissue adjacent to a tubular tissue to provide therapeutic hyperthermia which device has the capacity for high power.

It is yet another object of this invention to provide a catheter that can provide hyperthermia to tissue completely surrounding a tubular tissue.

These and other aspects of the invention can best be understood by examining the drawings and turning to the description of the preferred embodiments.

DETAILED DESCRIPTION OF THE INVENTION

Various medical procedures require the delivery of light energy to a target tissue causing a photoreaction (photochemical, photothermal, photoplasma, or photophysical). One such treatment involves the photocoagulation of the prostate tissue to treat Benign Prostate Hypertrophy (BPH). This malady is characterized by the uncontrolled proliferation of cells which make up the prostate gland in men. In its severe states it restricts the flow of fluids through the urethra. Lastly, it is also associated with a high incidence of prostate cancer.

Figure 15:
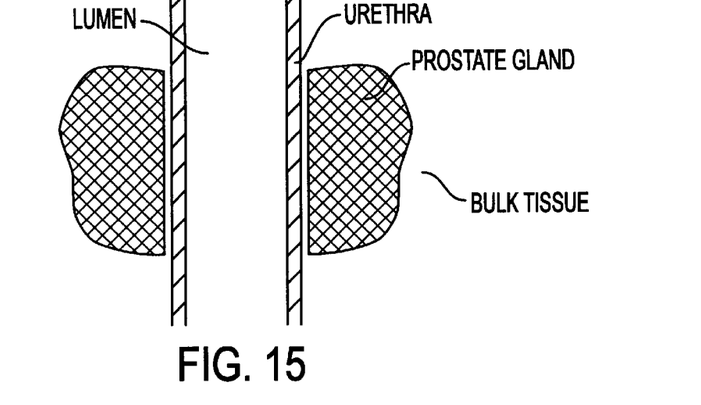
FIG. 15 is a cross-sectional view of a prostate gland surrounding the urethra.

Turning now to FIG. 15, the prostate is a gland which is generally toroidal in shape and surrounds the urethra. As the hypertrophy of the prostate cells occurs, the prostate swells and begins to constrict the urethra, thus restricting the flow of fluids through this tubular tissue. To treat this malady, surgical procedures such as TransUrethral Resection of the Prostate (TURP) are employed. Side effects include, incontinence, frequency of urination and impotence.

Figure 16A:
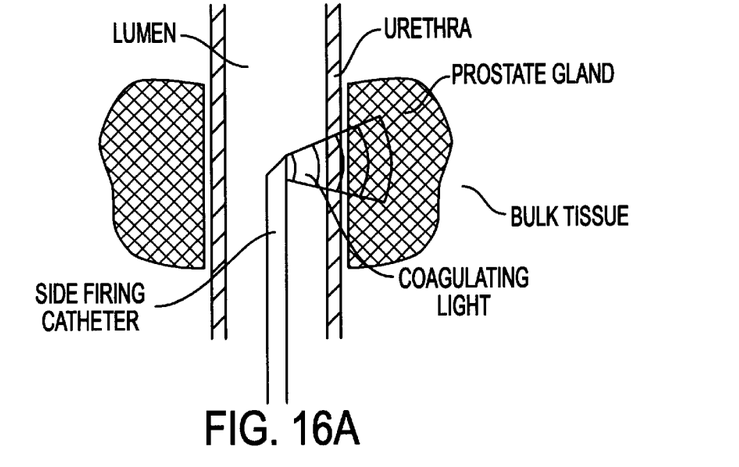
FIG. 16A is a cross-sectional view of a prostate gland showing the transluminal insertion of a side firing catheter into the urethra to irradiate the prostate.
Figure 16B:
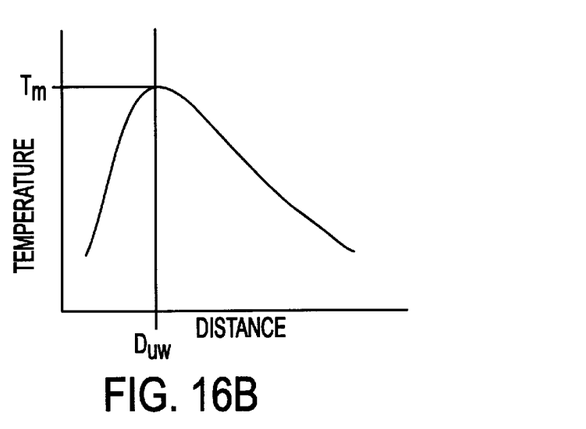
FIG. 16B shows the temperature distribution in the tissue immediately surrounding the urethra.

Recently hyperthermia has been employed as a treatment for BPH. A catheter is introduced intraluminally into the urethra. Light is delivered by a focusing fiber optic designed to emit light in a 45–90 degree direction to the axis of the catheter. This type of device creates temperature gradients in the irradiated tissue which is greatest at the interface closest to the delivery device. Referring to FIGS. 16A and 16B, the maximum temperature ($T_m$) occurs at the urethra wall ($D_{uw}$). If a catheter is placed in the urethra of a patient as shown in FIG. 16A, the resultant temperature gradient will appear as illustrated in FIG. 16B. Obviously, this will damage the healthy urethra to a greater extent compared to the diseased prostate.

By replacing the side firing light delivery device shown in FIG. 16A with a 360 degree cylindrical light diffusing device as shown in FIG. 16A, the therapy can be uniformly performed radially thus heating the entire prostate if needed. The device can also be partially shielded when heating the whole prostate is not desired. Using a cylindrical diffuser does not overcome the problem of heating the urethra to a greater extent than the prostate as previously discussed. Referring to FIG. 17B, $T_m$ again occurs at a distance $D_{uw}$, the urethra wall. Since $T_m$ is greater than the coagulation temperature, $T_c$ (or any other desired heating level), the urethra will coagulate before the prostate gland as is the case with the side firing system.

Figure 17A:
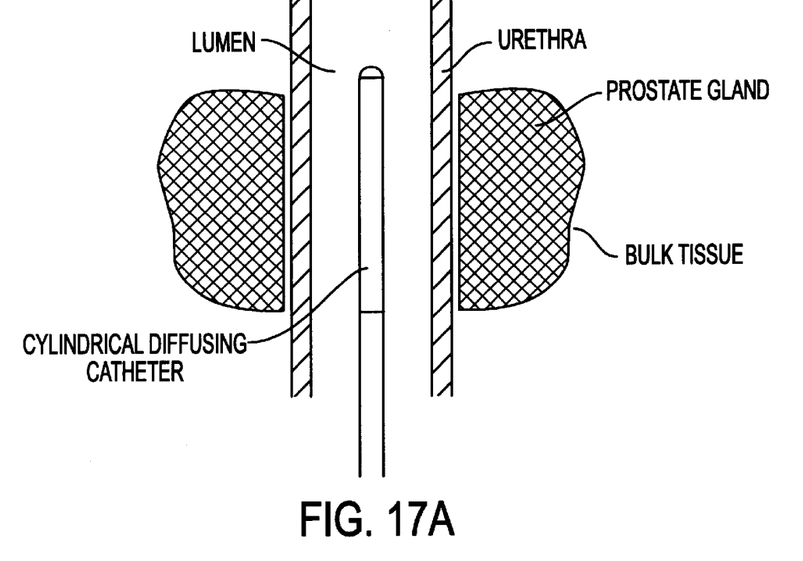
FIG. 17A is a cross-sectional view of the prostate gland with a more or less cylindrical diffuser tip inserted into the urethra.
Figure 17B:
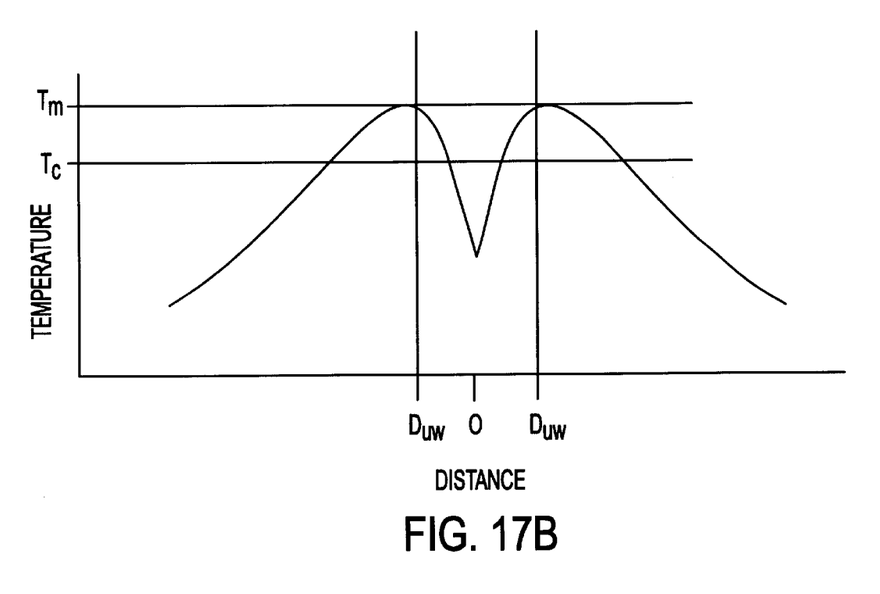
FIG. 17B shows the light distribution in the tissue surrounding the diffuser tip.
Figure 18A:
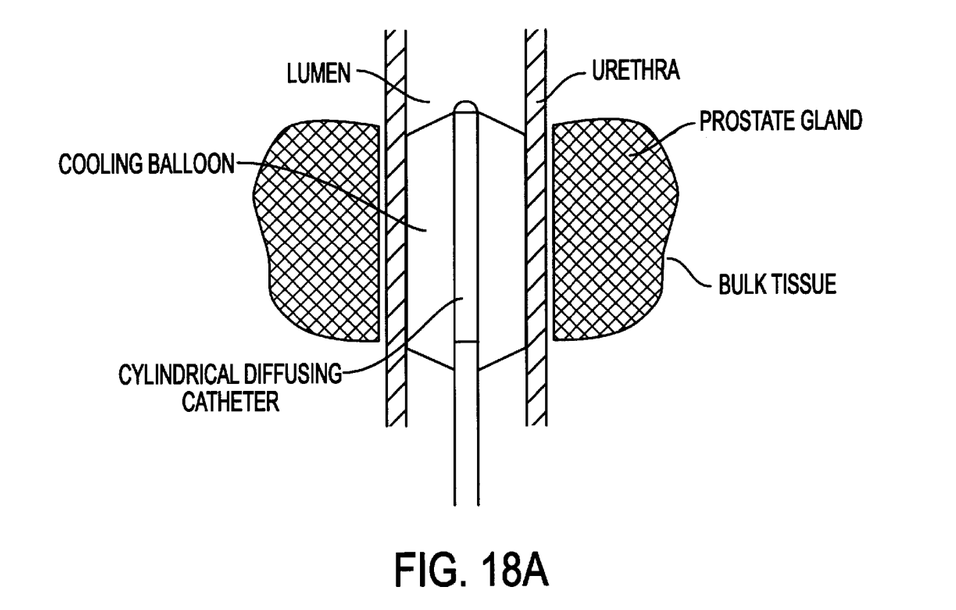
FIG. 18A is a cross-sectional view of the prostate gland showing a catheter according to the present invention inserted into the urethra and the cooling balloon is inflated.
Figure 18B:
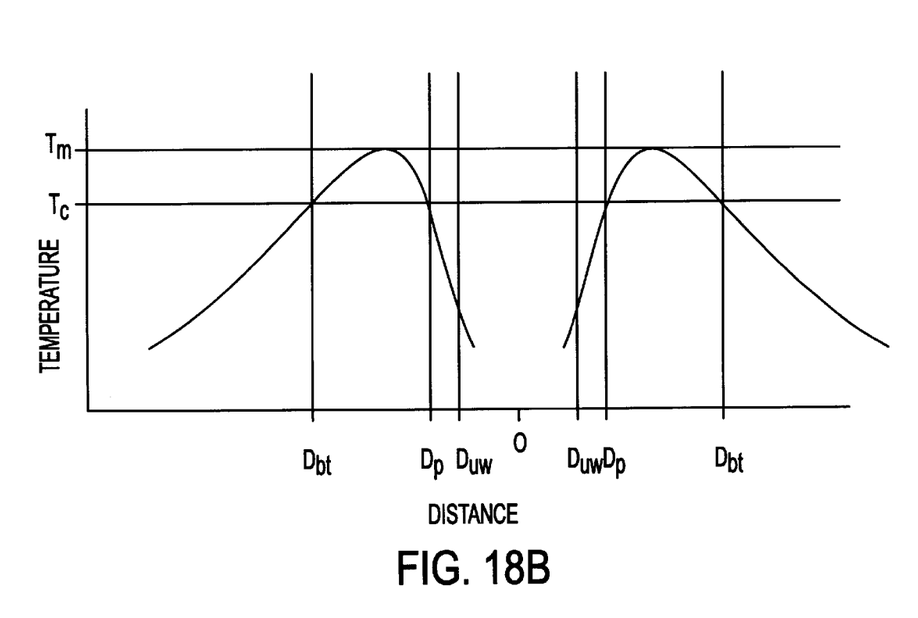
FIG. 18B shows the temperature distribution in the tissue surrounding the cooled diffuser tip of FIG. D1.

If a balloon is added to the device shown in FIG. 17A (see FIG. 18A) and cooling liquid is flowed through the balloon, the tissue at the interface, that is: the urethra wall; will be cooled by the flowing liquid, producing a temperature gradient as illustrated in FIG. 18B. The temperature between $D_{uw}$ and $D_p$ is below the threshold temperature for coagulation, $T_c$. The area between the prostate, $D_p$, and $D_{bp}$, the distance to where the bulk tissue beyond the prostate begins, reaches a temperature which is above the coagulation threshold, $T_c$. The maximum temperature, Tm is achieved well within the prostate.

The same type of balloon can be added to side firing systems to cool the tissues of the urethra causing deeper heating profiles. The balloon and coolant are, of course, optically transparent to the wavelengths used for inducing hyperthermia in the target tissue. Such a system may also be used for transilluminating the surrounding tisue for diagnostic purposes by keeping the maximum temperature $T_m$ below the coagualtion threshold $T_c$.

$T_c$ indicates the threshold temperature where coagulation occurs. If the temperature can be maintained below this threshold in both the urethral tissue and the non-target tissue beyond the prostate, the coagulation will be limited to the prostate, where it is intended. In addition to cooling the non-target urethral tissue, the fluid serves to cool the catheter diffuser tip allowing the device to be driven to much higher power levels without failure.

Figure 1:
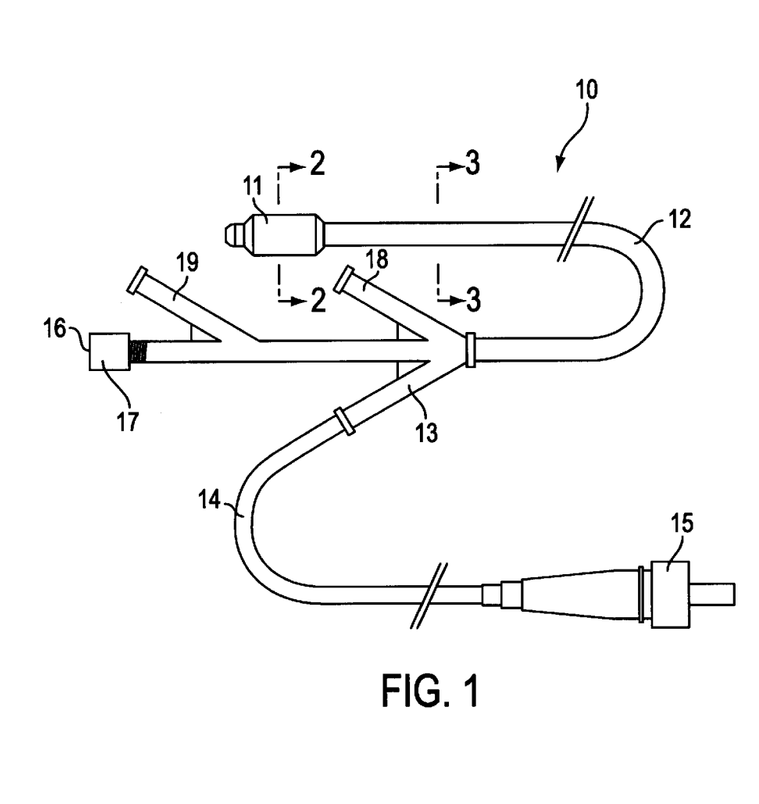
FIG. 1 is a schematic view of a hyperthermia catheter according to the present invention.

FIG. 1 illustrates the first preferred embodiment of a catheter, generally indicated at 10, employing the high power light diffuser. The distal portion of the catheter is surrounded by an optically clear, inflatable balloon 11 which is fitted to the catheter body 12. The internal components of the catheter body 12 are separated into three channels at the 3-way adapter 13. The fiber optic array (not shown) is directed into a bundle encased in a polymer tube 14 which delivers the bundle to the fiber optic connector 15. This connector 15 ultimately is coupled to the light source (not shown). The center arm of the 3-way adapter 13 houses the guidewire lumen 16 which is capped with a hemostasis valve 17. The third arm 18 of the 3-way adapter 13 provides an inlet for cooling fluid. The fluid is introduced through the infusion port 18 where it enters a dedicated channel (not shown) which in turn supplies the distal balloon 11 with cooling fluid while inflating the balloon 11. The fluid then enters a second dedicated channel (not shown) and returns the fluid to the 3-way adapter 13 where it is directed to the output port 19. The fluid is then directed from the output port 19 to an external closed loop chiller (not shown) where it is cooled and returned to the infusion port (18).

Figure 2:
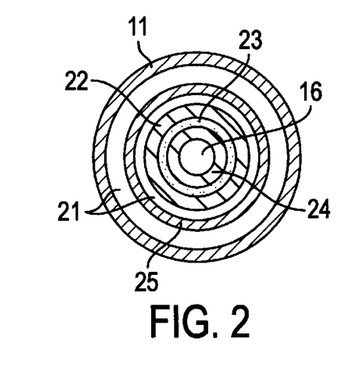
FIG. 2 is a cross-sectional view of the distal balloon taken along section line 2—2 of FIG. 1.

FIG. 2 illustrates the cross-sectional view of the distal balloon 11 taken at section line 2—2 in FIG. 1. The central guidewire lumen 16 is surrounded by the internal tube 24. The diffusing medium 23 is encased between the optically reflective internal tube 24 and the optically clear external tube 22. The balloon 11 is inflated with the inflation and coaling medium 21 and is concentrically located around the guidewire lumen 16. The optically clear fluid barrier tube 25 separates the inflation medium 21 into influx and effluent.

Figure 3:
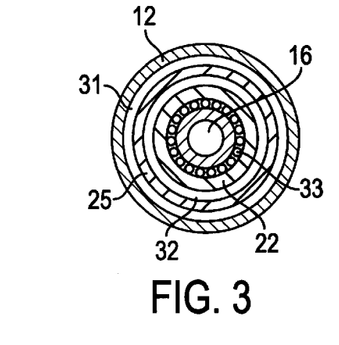
FIG. 3 is a cross-sectional view of the distal catheter body taken along section line 3—3 of FIG. 1.

FIG. 3 illustrates the cross-sectional view of the distal catheter body 12 taken at 3—3 in FIG. 1. The guidewire lumen 16 is surrounded by the internal tube 24 which in turn is surrounded by an array of fiber optics 33 which in turn is surrounded by the external tube 22 which in turn is surrounded by the dedicated infusion channel 32 which is surrounded by the fluid barrier 25 which in turn is surrounded by the dedicated output channel 31 which in turn is surrounded by the catheter body 12.

Figure 4:
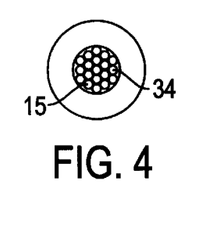
FIG. 4 is an end-on view of the proximal end of the catheter FIG. 1.

FIG. 4 is an end on view of the proximal end of the catheter 10. The fiber optic bundle 34 or a fused facsimile is housed in the stainless steel or similar material connector.

Figure 5:
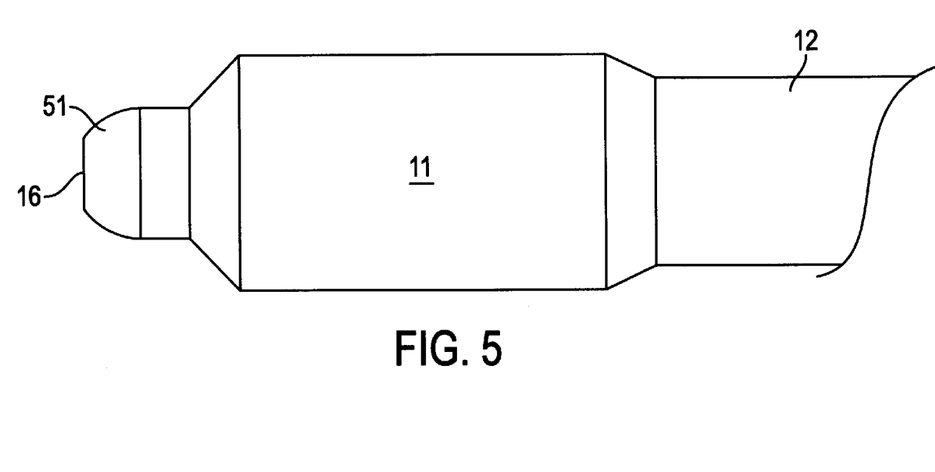
FIG. 5 is a close-up view of the distal end of the catheter including the balloon shown in FIG. 1.

FIG. 5 is a close up view of the balloon 11 shown in FIG. 1. The distal tip of the catheter 10 incorporates a rounded tip 51 for the atraumatic delivery of the device through the lumen of a tubular tissue such as the urethra or bronchus. The rounded tip 51 surrounds the guidewire lumen 16. Underlying the balloon 11 is the catheter body 12.

Figure 6:
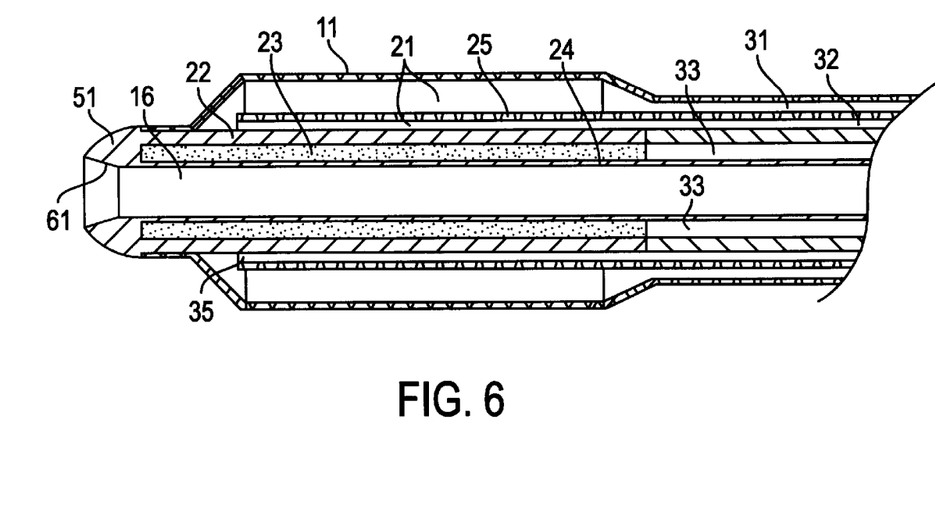
FIG. 6 is a longitudinal cross-sectional view of the distal end of the catheter shown in FIG. 5.

FIG. 6 is a cross-sectional view of the optically clear balloon 11 shown in FIG. 5. The rounded tip 51 creates the introducer funnel 61 which leads into the guidewire lumen 16. After the diffuser tip 23 is positioned intraluminally adjacent to the target tissue, the balloon 11 is inflated with a transparent inflation medium 21 which is supplied to the balloon through the dedicated infusion channel 32. The inflation medium exits the balloon through the dedicated output channel 31. The two channels are separated by a fluid barrier 25 except at a distal end to create a an opening 35. Light communication is achieved via an optical waveguide such as fiber optics 33 which conducts light from a source (not shown) such as a laser to the diffuser 23. The diffuser 23 is enclosed between an internal optically reflective tube (24) and the external optically clear tube 22.

Figure 7:
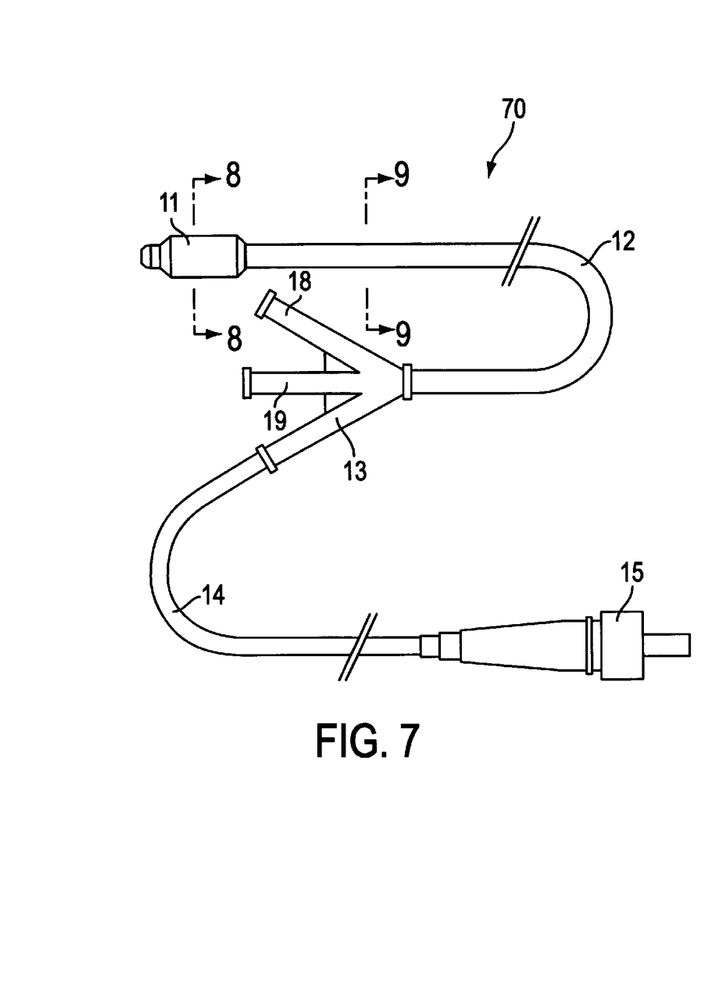
FIG. 7 is yet another embodiment of a high power light diffuser catheter.

FIG. 7 is a second embodiment of the high power light diffuser (70). The distal balloon 11 is attached to the catheter body 12 which in turn is connected to the 3-way adapter 13. The single fiber optic (not shown) is directed to the polymer tube (14) which in turn directs the single fiber optic to the fiber optic connector 15. The remaining two arms of the 3-way adapter 13 provide an infusion port 18 and an output port 19 for the inflation medium 21 connected by an external closed loop chiller (not shown).

Figure 8:
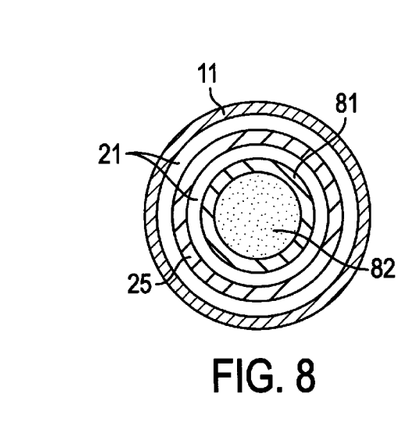
FIG. 8 is a cross-sectional view of the distal balloon taken at section line 8—8 of FIG. 7.

FIG. 8 illustrates the cross-sectional view of the distal balloon 11 taken at 8—8 in FIG. 7. The central diffusing medium 82 is surrounded by the optically clear diffuser sheath 81 which in turn is surrounded by the optically clear inflation medium 21 which in turn is surrounded by the optically clear balloon 11. The inflation medium 21 is separated into influx and effluent by the optically clear fluid barrier 25.

Figure 9:
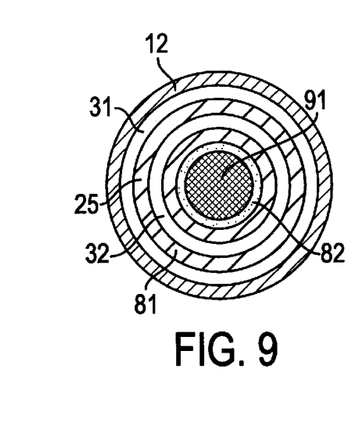
FIG. 9 is a cross-sectional view of the catheter body along section line 9—9 in FIG. 7.

FIG. 9 illustrates a cross-sectional view of the catheter body 12 taken at 9—9 in FIG. 7. The centrally located single fiber optic 91 is surrounded by the diffusing medium 82 which n turn is surrounded by the diffuser sheath 81 which in turn is surrounded by the dedicated infusion channel 32 which in turn is surrounded by the optically clear fluid barrier 25 which in turn is surrounded by the dedicated output channel 31 which in turn is surrounded by the catheter body 12.

Figure 10:
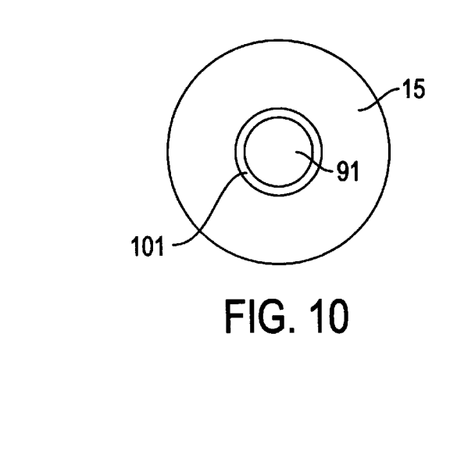
FIG. 10 is an end-on view of the proximal catheter.

FIG. 10 is an end on view of the proximal catheter 70. The single fiber optic 91 is surrounded by epoxy 101 which in turn is surrounded by the fiber optic connector 15.

FIGS. 11–14 represent four embodiments of the distal balloon shown in FIG. 7.

Figure 11:
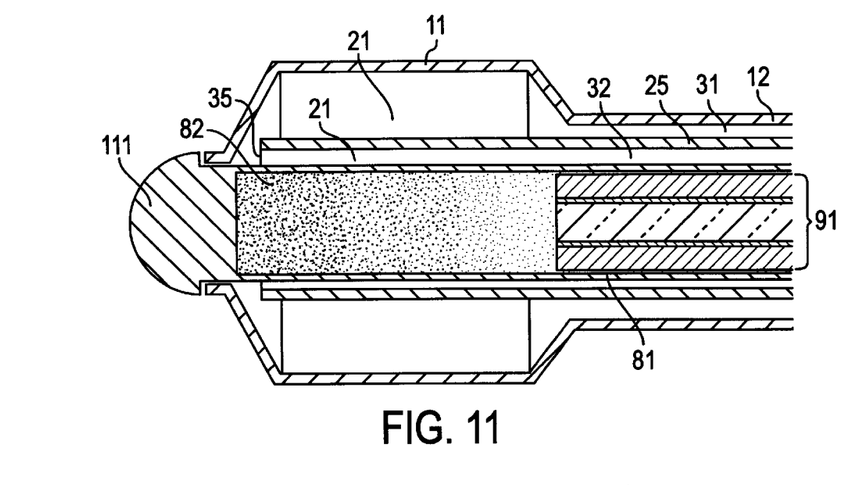
FIG. 11 is a longitudinal cross-sectional view of the first embodiment of the catheter shown in FIG. 7.

FIG. 11 is a cross-sectional view of the distal catheter shown in FIG. 7. The distal hemispherical tip 111 allows for the atraumatic delivery of the device. The balloon 11 is inflated with the inflation medium 21 which is delivered to the balloon 11 through the dedicated infusion channel 32 and exits the balloon 11 through the dedicated output channel 31. The two channels are separated by the optically clear fluid barrier 25. The balloon is attached proximally to the catheter body 12. Light communication is provided via the single fiber optic 91 from the source (not shown) to the diffusing medium 82.

Figure 12:
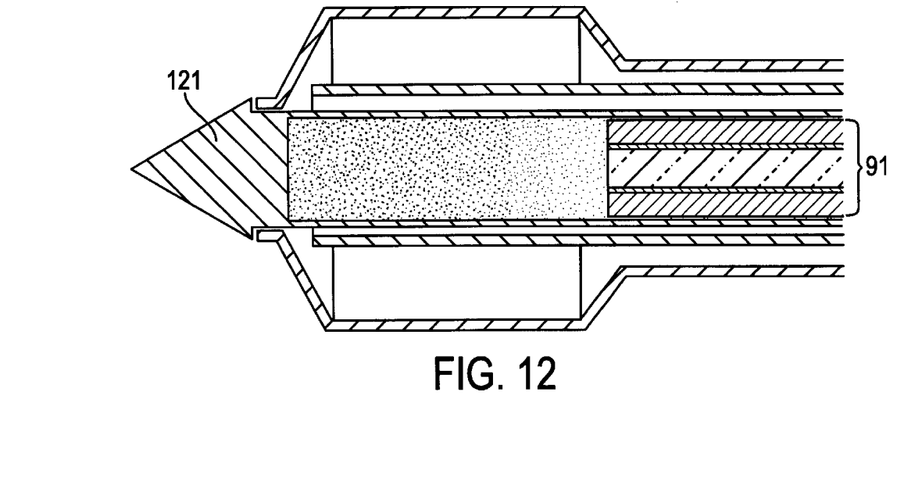
FIG. 12 is a cross-sectional view of a second preferred embodiment of the balloon portion of the catheter shown in FIG. 7.

FIG. 12 is a cross-sectional view of the distal catheter shown in FIG. 7. The distal tip is identical to that shown in FIG. 11 with the exception that the hemispherical tip (111 in FIG. 11) is replaced with a conical tip 121 for interstitial insertion of the device.

Figure 13:
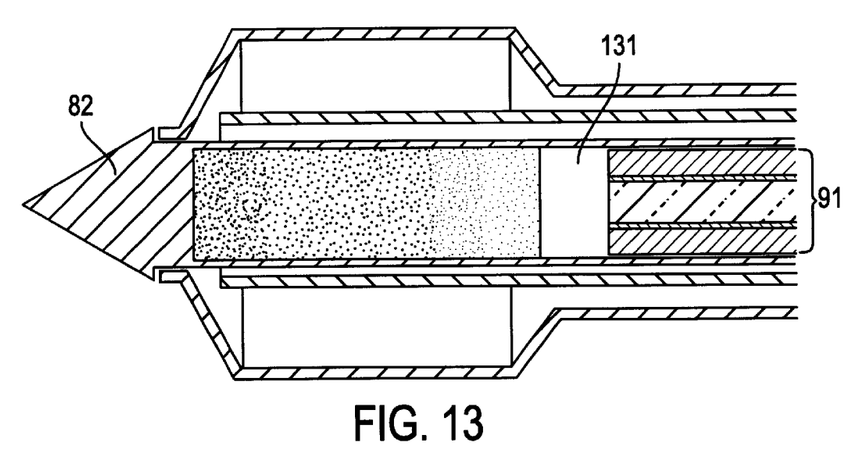
FIG. 13 is a longitudinal cross-sectional of a third preferred embodiment of the balloon shown in FIG. 7.

FIG. 13 is a cross-sectional view of the distal catheter shown in FIG. 7. The distal tip is identical to that shown in FIG. 12 with the exception of a fluid (gas or liquid) gap 131 placed between the fiber optic 91 and the diffusing medium 82.

Figure 14:
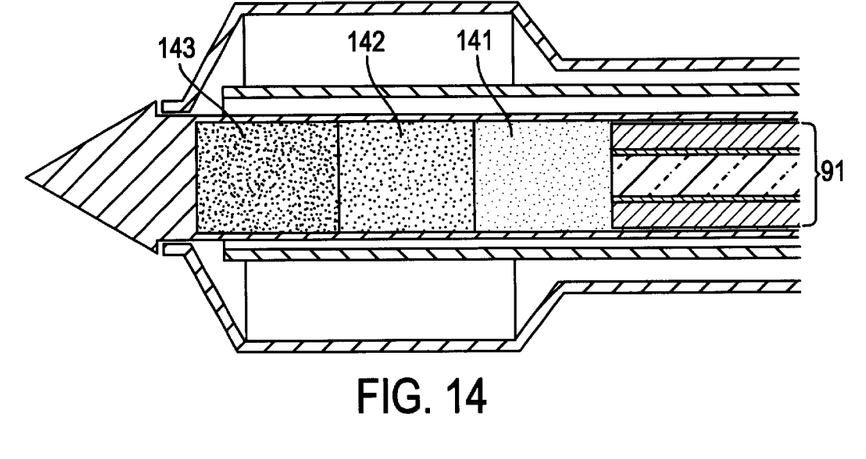
FIG. 14 is a longitudinal cross-sectional view of yet another embodiment of the distal tip of the hyperthermia catheter including the balloon shown in FIG. 7.

FIG. 14 is a cross-sectional view of the distal catheter shown in FIG. 7. The distal tip is identical to that shown in FIG. 12 with the exception of replacing the continuous gradient diffusing medium (82 in FIG. 12) with multiple discrete diffusing segments. The diffusing segment 141 closest to the fiber optic 91 has the lowest concentration of scattering centers in elastomer substrate (as low as zero) of all the segments. The second segment 142 has the next lowest concentration of scatter centers in elastomer substrate. The same trend continues with the third segment 143 and the fourth (now shown), etc. While it is not shown, an outer layer of elastomer or elastomer plus scattering centers may be used to create the desired optical output of the device.

The catheter may be used for inducing hyperthermia in prostate tissue as follows:

1. The catheter is advanced through the urethra until the balloon and underlying diffuser are positioned in the urethra adjacent to and centered within the prostate (the target tissue).
2. The balloon is inflated to intimately contact the internal wall of the urethra.
3. The inflation of the balloon is maintained by circulating a cooling fluid through the catheter to and from the interior chamber of the balloon. The fluid exits the catheter where it is transported to an external chiller. After the fluid has been cooled to body temperature or slightly below body temperature, the fluid is returned to the balloon through the catheter. This process continues in a closed loop.
4. Light is then delivered to the tip and emitted radially (focused or diffused) to the target tissue.
5. Following coagulation or lower level heating of the prostate tissue, the light is extinguished, the fluid is terminated thus deflating the balloon, and the delivery device is removed from the urethra.

While the utility of the device has been demonstrated using the hyperthermia treatment of BPH as an example, it should not be construed that this device is limited to that application. The use of this device to adjunctively treat other hyperproliferative cells such as esophageal tumors with PDT or selective hyperthermia or a combination of the two is an obvious extension of the utility of the cooled catheter. The same device in a spherical geometry could be used to treat bladder cancer, or illuminating the tissue surrounding the cavity remaining after the resection of a tumor or other mass. BPH can also be treated with PDT. Since studies show that photosensitizers are concentrated in the deeper tissues of the prostate, the incorporation of a cooling means around the diffused tip would facilitate the procedure by allowing the diffuser to be driven at higher powers and by providing more efficient and safer hyperthermia simultaneously with PDT, which has shown a strong synergism.

In addition to the aforesaid therapeutic applications red light is particularly useful for performing transillumination of tissue for diagnostic purposes. This is due to the relative lucency of blood and tissue to light at longer wavelengths. Such light must be delivered at a power level sufficient to penetrate the tissue under investigation and be detected. Light delivery tips suitable for transillumination may be placed beneath the skin. A transparent balloon surrounding the diffuser tip may then be inflated with a cooling fluid to expand against the surrounding tissue. Cooling the tissue adjacent to the diffuser tip by thermal contact with the heat-conducting fluid circulating through the interior of the transparent balloon will permit the delivery of transilluminating light at greater power levels without tissue destruction. In this regard, a material having good heat conduction characteristics is a preferred material for balloon wall construction.

Representative and preferred embodiments of the invention having been described and illustrated, it is to be understood that, within the scope of the appended claims, various changes can be made therein. Hence, the invention can be practiced in ways other than those specifically described herein. For example, the catheter may be used for interstitial induction of hyperthermia in a target tissue when it is necessary or desirable to prevent overheating of the tissue immediately adjacent to the diffusive light source. It is clear that the principal of using a transparent heat conducting balloon around a light delivery diffuser tip to cool the adjacent tissue during photoirradiation can be applied to a variety of geometries. As a further example; if, following the excision of a tissue, it is advantageous to photoirradiate the tissue surrounding the excised tissue. A transparent balloon of any suitable shape can be inserted into the void space left by the excised tissue and filled with a volume of coolant sufficient to expand the balloon against the surrounding walls. A light diffuser tip positioned within the interior of the inflated balloon may then be used to photoirradiate the surrounding tissue.

What we claim is:

1. A light delivery catheter having a proximal end and an invasive distal end comprising a light diffuser tip operable for delivering diffuse phototherapeutic light to a target tissue without causing substantial heating of non-target tissue wherein said non-target tissue is situated between the light diffuser tip on the catheter and the target tissue, said catheter having an elongate body portion between said proximal end and said distal end and two coolant circulating lumens, said two coolant circulating lumens having a proximal end and a distal end and being coaxially disposed within said body portion of said catheter and being separated from each other by a fluid barrier wall except at an opening in said distal end which opening provides fluid communication between said two coolant circulating lumens, and an optical waveguide substantially coextensive with said elongate body portion and wherein the optical waveguide has a proximal light receiving end and a distal light output end which light output end terminates in said diffuser tip which is operable for directing light out of said optical waveguide, and an inflatable optically transparent balloon coaxial with and exterior to said body portion and coextensive with and surrounding said diffuser tip, and a coolant fluid reservoir containing an optically transparent coolant, the interior of said balloon being in fluid communication with said two coolant circulating lumens and being inflatable when a coolant fluid is injected into said interior of said balloon via said opening and wherein said proximal ends of said two coolant circulating lumens have means thereon adapted for fluid connection to said coolant fluid reservoir.

2. The catheter of claim 1 wherein said balloon diffuser comprises an optically transparent elastomer.

3. The catheter of claim 1 wherein said balloon comprises a substantially optically transparent elastomer.

4. The light delivery catheter of claim 1, wherein the fluid barrier wall is optically clear.

5. A light delivery catheter for delivering diffuse phototherapeutic light to a target tissue without causing substantial heating of non-target tissue, the catheter comprising:

an elongate body portion having a distal end and a proximal end;

an invasive distal portion at the distal end of the elongate body portion comprising a light diffuser tip operable for directing light incident thereon out of the catheter to illuminate the target tissue when the non-target tissue is situated between the light diffuser tip and the target tissue;

an optical waveguide substantially coextensive with the elongate body portion and having a proximal light receiving end and a distal light output end adapted to direct light emanating therefrom to impinge upon said diffuser tip;

a coolant and inflation fluid inlet lumen, and a coolant and inflation fluid outlet lumen coextensive with a portion of said body portion of said catheter, the coolant and inflation fluid inlet and outlet lumens being coaxially oriented with respect to each other in the catheter and separated, except at a distal end to create an opening, by a coaxial fluid barrier wall; and an inflatable optically transparent balloon coaxial with and exterior to the elongate body portion and coextensive with and surrounding the diffuser tip, the inflatable optically transparent balloon providing a coolant fluid interior chamber adapted for receiving an optically transparent coolant and inflation fluid and being inflatable therewith, the interior chamber of said balloon being in fluid communication with the coolant and inflation fluid inlet and outlet lumens via the opening at the distal end of the barrier wall, and wherein said proximal ends of the coolant and inflation fluid inlet and outlet lumens have means thereon adapted for fluid connection with a coolant fluid reservoir to allow for circulation of the coolant and inflation fluid between the coolant fluid reservoir and the interior chamber of the balloon.

6. The light delivery catheter of claim 5, further comprising a rounded tip at a distal end of the catheter.

7. The light delivery catheter of claim 5, further comprising a conical tip at a distal end of the catheter.

8. The light delivery catheter of claim 5, wherein a fluid gap is located between the optical waveguide and the diffuser tip.

9. The light delivery catheter of claim 5, wherein the diffuser tip comprises multiple discrete light diffusing segments.

10. The light delivery catheter of claim 5, wherein the coolant and inflation fluid inlet lumen is positioned coaxially inwardly of the coolant and inflation fluid outlet lumen.

11. The light delivery catheter of claim 5, wherein the diffuser element is a side firing fiber optic.

12. The light delivery catheter of claim 5, wherein the fluid barrier wall is optically clear.

13. A light delivery catheter for delivering diffuse phototherapeutic light to a target tissue without causing substantial heating of non-target tissue, the catheter comprising:

an elongate body portion having a distal end and a proximal end;

an invasive distal portion at the distal end of the elongate body portion comprising a light diffuser tip operable for directing light incident thereon out of the catheter to illuminate the target tissue when the non-target tissue is situated between the light diffuser tip and the target tissue;

an optical waveguide substantially coextensive with the elongate body portion and having a proximal light receiving end and a distal light output end adapted to direct light emanating therefrom to impinge upon said diffuser tip;

a coolant and inflation fluid inlet lumen, and a coolant and inflation fluid outlet lumen coextensive with a portion of said body portion of said catheter, the coolant and inflation fluid inlet and outlet lumens being coaxially oriented with respect to each other in the catheter and separated, except at a distal end to create an opening, by a coaxial fluid barrier wall;

an inflatable optically transparent balloon coaxial with and exterior to the elongate body portion and coextensive with and surrounding the diffuser tip, the inflatable optically transparent balloon providing a coolant fluid interior chamber adapted for receiving an optically transparent coolant and inflation fluid and being inflatable therewith, the interior chamber of said balloon being in fluid communication with the coolant and inflation fluid inlet and outlet lumens via the opening at the distal end of the barrier wall, and wherein said proximal ends of the coolant and inflation fluid inlet and outlet lumens have means thereon adapted for fluid connection with a coolant fluid reservoir to allow for circulation of the coolant and inflation fluid between the coolant fluid reservoir and the interior chamber of the balloon; and a central guidewire lumen for receipt of a guidewire, and wherein the optical waveguide substantially surrounds the guidewire lumen.

14. The light delivery catheter of claim 13, further comprising a rounded tip at a distal end of the catheter.

15. The light delivery catheter of claim 13, further comprising a conical tip at the distal end of the catheter.

16. The light delivery catheter of claim 13, wherein a fluid gap is located between the optical waveguide and the diffuser tip.

17. The light delivery catheter of claim 13, wherein the diffuser tip comprises multiple discrete light diffusing segments.

18. The light delivery catheter of claim 13, wherein the coolant and inflation fluid inlet lumen is positioned coaxially inwardly of the coolant and inflation fluid outlet lumen.

19. The light delivery catheter of claim 13, wherein the diffuser element is a side firing fiber optic.

20. The light delivery catheter of claim 13, wherein the fluid barrier wall is optically clear.

21. A method of selectively heating target tissue in the body of a patient wherein said target tissue is located adjacent to a tubular tissue in the body of said patient, said tubular tissue having a lumen coextensive therewith, said method comprising the steps of:

(a) inserting the distal tip of a catheter according to claim 1 into the lumen of said tubular tissue and advancing said distal tip until the diffuser element is adjacent to said target tissue;

(b) inflating said balloon with a coolant fluid until the balloon presses against the wall of said lumen; and (c) circulating said coolant fluid through a means for cooling said coolant to a predetermined temperature; and (d) illuminating said target tissue with an amount of light sufficient to achieve a therapeutic effect within said target tissue.

22. The method of claim 21 further comprising the step of administering a photosensitizer molecule into said target tissue prior to illuminating said target tissue.

23. A method of selectively heating target tissue in the body of a patient wherein said target tissue is located adjacent to a cavity in the body of said patient, said method comprising the steps of:

(a) inserting the distal tip of a catheter according to claim 1 into said cavity until the light diffuser element is adjacent to said target tissue;

(b) inflating said balloon with a coolant fluid until the balloon presses against the wall of said cavity; and (c) circulating said coolant fluid through a means for cooling said coolant to a predetermined temperature; and (d) illuminating said target tissue with an amount of light sufficient to achieve a therapeutic effect in said target tissue.

24. The method of claim 23 further comprising the step of introducing a photosensitizer molecule into said target tissue prior to illuminating said target tissue.

* * * * *